(12) United States Patent
Fraser

(10) Patent No.: US 8,769,753 B2
(45) Date of Patent: Jul. 8, 2014

(54) ULTRASONIC TEETH CLEANING APPLIANCE HAVING SPATIAL, TEMPORAL AND/OR FREQUENCY VARIATIONS

(75) Inventor: John Douglas Fraser, Woodinville, WA (US)

(73) Assignee: Koninklijke Philips N.V., Eindhoven (NL)

( * ) Notice: Subject to any disclaimer, the term of this patent is extended or adjusted under 35 U.S.C. 154(b) by 106 days.

(21) Appl. No.: 13/141,551

(22) PCT Filed: Dec. 9, 2009

(86) PCT No.: PCT/IB2009/055611
§ 371 (c)(1),
(2), (4) Date: Jun. 22, 2011

(87) PCT Pub. No.: WO2010/076705
PCT Pub. Date: Jul. 8, 2010

(65) Prior Publication Data
US 2011/0256503 A1    Oct. 20, 2011

Related U.S. Application Data

(60) Provisional application No. 61/141,330, filed on Dec. 30, 2008.

(51) Int. Cl.
*A61C 17/20* (2006.01)
(52) U.S. Cl.
USPC .............. 15/22.1; 15/167.1; 433/119

(58) Field of Classification Search
USPC .......... 15/22.1, 105, 167.1; 433/119
See application file for complete search history.

(56) References Cited

U.S. PATENT DOCUMENTS

| | | | |
|---|---|---|---|
| 3,696,809 A | 10/1972 | Moret | |
| 3,809,977 A | 5/1974 | Balamuth et al. | |
| 3,828,770 A | 8/1974 | Kuris et al. | |
| 5,138,733 A | 8/1992 | Bock | |
| 6,309,355 B1 * | 10/2001 | Cain et al. | 600/439 |
| 7,269,873 B2 | 9/2007 | Brewer et al. | |
| 2005/0196725 A1 | 9/2005 | Fu | |
| 2008/0168611 A1 | 7/2008 | Lilley et al. | |
| 2009/0211042 A1 * | 8/2009 | Bock | 15/22.1 |

FOREIGN PATENT DOCUMENTS

| | | |
|---|---|---|
| WO | 9210146 | 6/1992 |
| WO | 2007060644 A2 | 5/2007 |
| WO | 2009047670 A2 | 4/2009 |

* cited by examiner

*Primary Examiner* — Randall Chin

(57) ABSTRACT

The appliance includes an appliance body (12) as well as a system for producing microbubbles (20) and a system for producing an ultrasound signal beam (22) in a frequency range which activates at least some of the microbubbles. The appliance includes at least one of the following: (a) an array of ultrasound transducer elements (40) which produce a plurality of ultrasound signal beams; (b) an amplitude modulation assembly (51) for modulating the amplitude of the ultrasound signal; and (c) a frequency modulation system (61) for changing the frequency of the ultrasound signals over a selected range, to impact a range of microbubble sizes.

15 Claims, 4 Drawing Sheets

ULTRASONIC TEETH CLEANING APPLIANCE HAVING SPATIAL, TEMPORAL AND/OR FREQUENCY VARIATIONS

TECHNICAL FIELD

This invention relates generally to dental appliances, such as toothbrushes, both power and manual, and also to mouthguards for cleaning teeth, and more specifically concerns such appliances which include the use of ultrasound and microbubbles to provide or improve cleaning effects.

BACKGROUND OF THE INVENTION

Ultrasound-induced cavitation of air microbubbles to clean biofilm off of teeth surfaces, as well as below the gum line, is generally known. An example of such ultrasonic technology is shown in U.S. Pat. No. 5,138,733 to Bock. Other examples include U.S. Pat. No. 3,809,977 to Balamuth and U.S. Pat. No. 7,269,873 to Brewer et al. Further, there have been commercial dental appliances which utilize an ultrasound/microbubble approach to cleaning teeth. Such appliances, however, typically have one or more significant disadvantages.

First, while the cleaning action produced by cavitation of the microbubbles generally can be strong in the vicinity of some of the bubbles, not all of the bubbles are strongly active, and even the ones which are active tend to remain in a single position longer than necessary to clean an area around that position. Overall cleaning action is thus believed to be weaker than otherwise could be the case with the typical number of bubbles available and with the same ultrasound excitation.

Further, cleaning is spotty on a macroscopic level. Certain regions on the surfaces of the teeth will exhibit strong cleaning, while others exhibit almost no cleaning at all. This is possibly due to variations in ultrasound intensity caused by interference effects due to reflection of the ultrasound off the various teeth surfaces.

Still further, adequate bubble concentration is difficult to maintain in the teeth recesses where the cavitation could actually have the most beneficial effect, because of ineffective cleaning by scrubbing. This lack of bubble concentration is likely due to the destruction of bubbles by the same ultrasound which would ordinarily produce cleaning.

Accordingly, an ultrasound/microbubble system is desired to either complement existing manual or power toothbrushes or mouthpieces, or to be used alone in order to produce a significant cleaning effect on the teeth, along the gum line and in the interproximal areas of the teeth.

SUMMARY OF THE INVENTION

Accordingly, such an appliance comprises a system for producing ultrasound signal beams with a frequency in the range of 100 KHz to 1 MHz, directed to and actuating the microbubbles for cleaning, wherein the system for producing the ultrasound signals includes at least one of the following: (a) an array of transducer elements to produce the ultrasound signals; (b) an amplitude modulation assembly for modulating the amplitude of the ultrasound signals; and (c) a frequency modulation system for changing the frequency of the ultrasound signals over a predetermined range.

DETAILED DESCRIPTION OF THE INVENTION

As indicated above, dental appliances, particularly toothbrushes, incorporating an ultrasound/microbubble system to assist in the cleaning of teeth, are known, as discussed in the above patents and in other patents and patent publications. Typically, in those known systems, the ultrasound signal is limited to a single frequency with a consistent signal strength. The system described herein, however, incorporates a capability of one or more of the following features: (1) an array of transducer elements to provide more than one source position and/or direction for the ultrasound beam; (2) amplitude modulation of the ultrasound signals in order to allow new bubbles to repopulate a region in which cleaning has just occurred; and (3) frequency modulation of the ultrasound signals to produce a continuing variation of frequency over a specified range. Further, another feature is the use of phase modulation, i.e. changing the phase of the ultrasound signals, to steer and focus the ultrasound signals.

Each of the above features are described in more detail below. An operative appliance system may include one or two or all of the above features.

It should be understood that the present system can be used in a conventional toothbrush, with or without bristles, as well as a mouthguard/mouthpiece, again, with or without bristles. The appliances can be either manually operated or power operated.

If bristles are included, which would provide a traditional scrubbing action from the overall toothbrush action, the ultrasound/microbubble features produce an improvement in the performance of the resulting dental appliance. The dental appliance, however, could alternately be used with just the ultrasound/microbubble features described herein.

Figure 1:
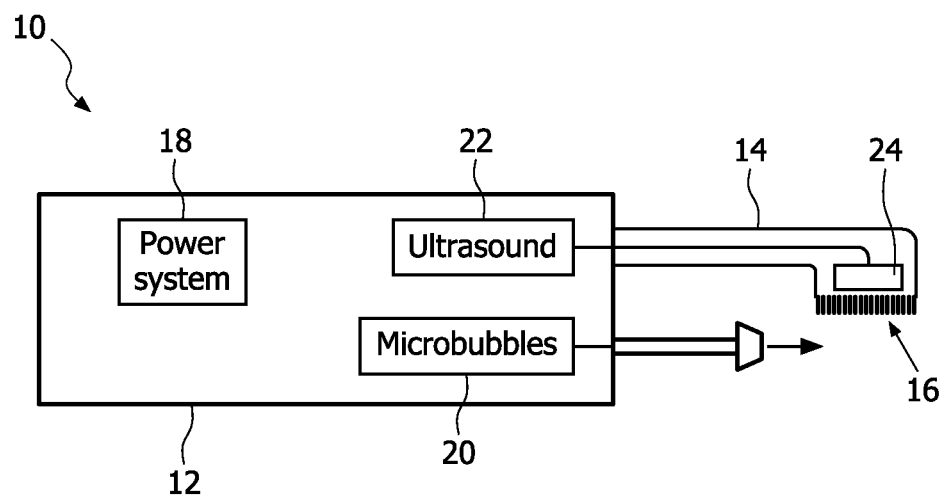
FIG. 1 is a general pictorial view of a toothbrush incorporating the present ultrasound/microbubble invention.

Briefly, the toothbrush of FIG. 1, shown generally at 10, includes a body portion 12 and an extending arm/brushhead portion 14. Brushhead portion 14 in FIG. 1 includes a bristle field 16 but, as indicated above, a bristle field is not essential. If the toothbrush is a power toothbrush, the body portion will include a power system, shown generally at 18, which will include a motor/driver, a power source and a control unit for moving the brushhead. FIG. 1 also includes a system for producing microbubbles 20, typically on the order of 1 µm-150 µm in size, although the size can vary beyond this range, which could also be produced by an external device, and an ultrasound unit 22 and transducer elements in the form of an array 24 which produces an ultrasound field, acting on the microbubbles which are located adjacent the dental surfaces to be cleaned.

Figure 2:
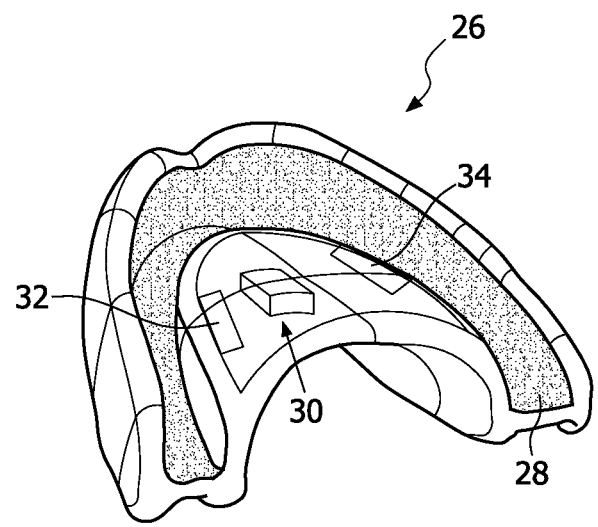
FIG. 2 is a general pictorial view of a mouthpiece incorporating the present ultrasound/microbubble invention.

FIG. 2 shows a mouthpiece generally at 26, which may or may not have a set of bristles 28 for cleaning the upper and lower teeth by scrubbing. The bristles 28 are mounted on the teeth-facing surfaces of mouthpiece 26. The mouthpiece may be manually operated by the user simply moving the teeth, or it can be power-operated by a power system shown generally at 30, which includes a motor to move the mouthpiece and the bristles in a prescribed manner. In the present system, the mouthpiece will also include a conventional system for producing microbubbles, or the microbubbles could be produced externally, directed to the vicinity of the teeth to be cleaned, and an ultrasound system, also conventional, for producing ultrasound signals to activate the microbubbles for cleaning shown representationally at 32 and 34, respectively.

Figure 3:
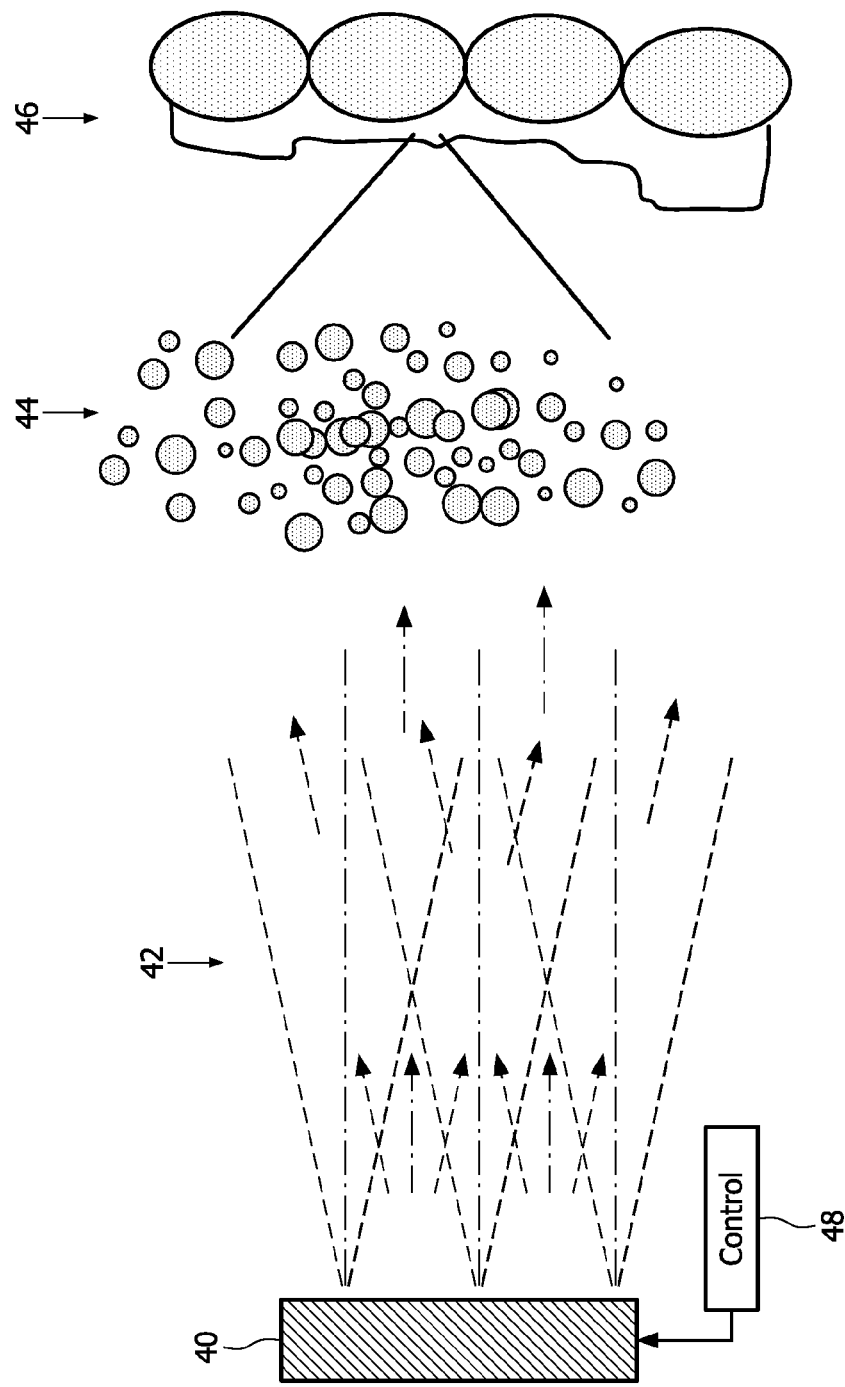
FIG. 3 is a diagram showing a spatial diversity arrangement for the ultrasound/microbubble system.

FIG. 3 shows a system which is optionally a part of the dental appliance of either FIG. 1 or FIG. 2. FIG. 3 concerns a spatial diversity arrangement for the ultrasound signal beams. Instead of a single radiator/transducer, the system includes an array of elements, shown generally as a group at 40. The array can include as few as three separate elements, but six to eight elements are preferred, although more elements could be used, e.g. 16, as well. The ultrasonic array 40 produces a plurality of ultrasound beams 42 which are directed toward the microbubble slurry, shown at 44, in the vicinity of the teeth 46 to be cleaned. With an electrical control 48, the individual ultrasound beams can be directed randomly or cyclically to various parts of the teeth surfaces at various angles, over a selected period of time, as opposed to being fixed in direction and time. The individual elements can be controlled separately, with a steering capability for each beam, or the entire array can be steered as a unit, or portions thereof can be steered/controlled independently of other portions. Steering is accomplished through phase modulation of the ultrasound signals, by control unit 48.

The individual elements can also be driven, i.e. powered, separately, so that they are not all on or off at the same time. By use of the steering capability, the ultrasound signals may be applied to the bubbles from different angles/directions. This can be accomplished over a specific time in a particular way which is compatible to the lifetime of the microbubble, so that as the bubbles in one single region are exhausted, and the beams steered for treatment of a new region, fresh bubbles can repopulate the original region. The variation in position and direction of the ultrasound beams will also result in a reduction of the variance in the interference effects, allowing the locations of strong cleaning to "sweep over" entire tooth surfaces, rather than missing spots.

Hence, with a plurality of elements, individual and/or group control over their on/off status and their direction, a significant improvement in consistency and quality of cleaning is achieved. Further, with respect to the beam steering capability, in particular, the toothbrush need not be moved to produce an effective, controlled movement of the beam.

Figure 4:
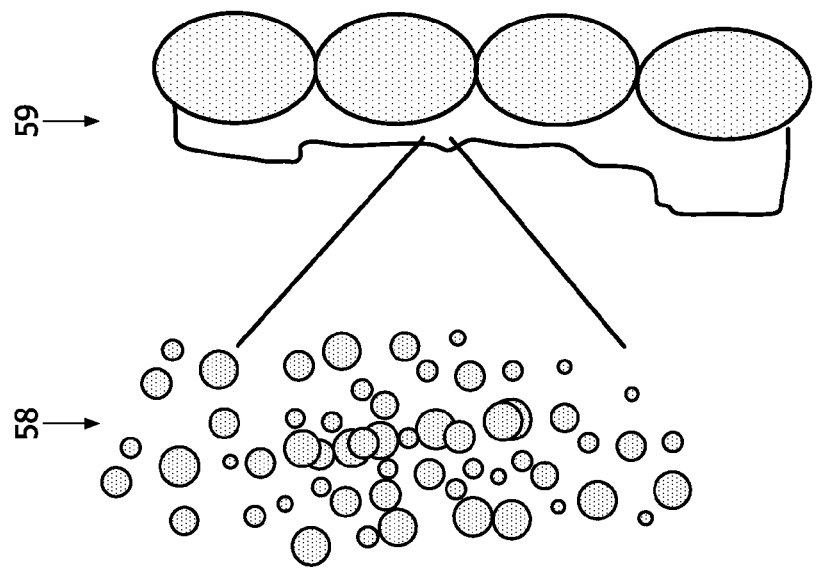
FIG. 4 is a diagram showing a temporal diversity (amplitude modulation) arrangement for the ultrasound/microbubble system.
Figure 4:
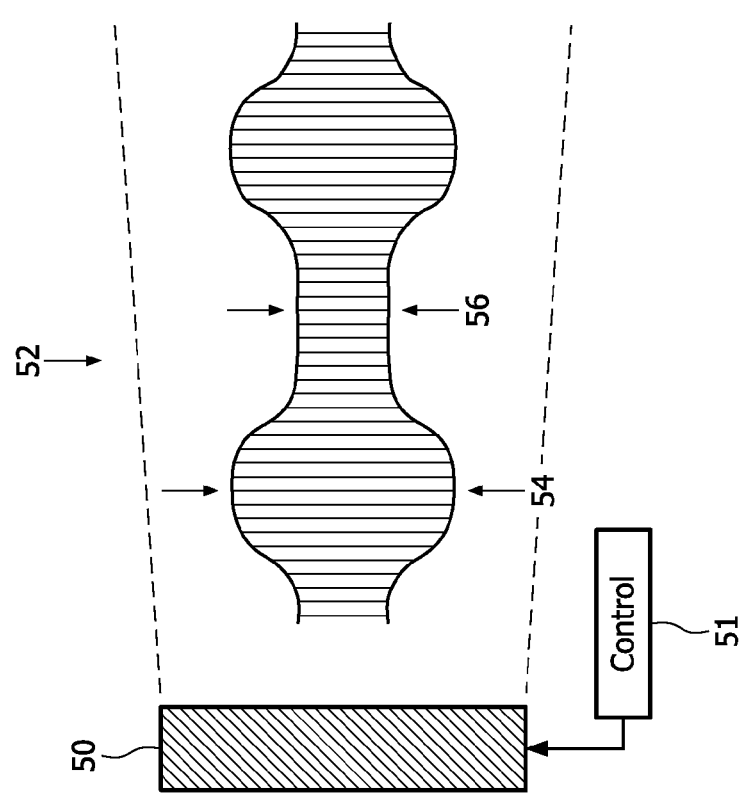

FIG. 4 illustrates a temporal diversity capability of the overall system, i.e. amplitude modulation of the ultrasound beams. This is a time-varying change in the amplitude of the excitation of the ultrasound transducer, provided in control unit 51. Given the finite lifetime of a microbubble, it is necessary to decrease the amplitude of excitation in a specific cleaning region from time to time to allow fresh bubbles to repopulate that region. However, during this time, the ultrasound signal is not turned completely off by the modulation signal, but rather maintains an amplitude which is sufficient for streaming of the fluid bathing the teeth, which assists in the distribution of bubbles in the slurry to new spots which have not yet been cleaned.

When the ultrasound beam(s) are focused on a given spot for cleaning, the bubbles which are the right size relative to the ultrasound to clean become depleted after a time. With amplitude modulation, beam power is decreased repeatedly to let the bubbles replenish in the region. The frequency of the amplitude modulation is much lower than the ultrasound frequency itself. For example, a 10 KHz modulation frequency is used for a 1 MHz ultrasound frequency. It is important that when the power is at a low level due to the amplitude modulation, it is still high enough that the streaming effect is still present, which transports a distribution of bubbles to new areas and to areas which are depleted.

For a lower ultrasound frequency, e.g. 100 KHz, the modulating signal could be 100 Hz, although 10 Hz also would also likely be useful.

The amplitude modulation should decrease the power (the ultrasound signal strength) by at least 50%, but as indicated above, not to zero, to preserve the streaming effect. In the system of FIG. 4, there is shown a transducer or transducer array, generally at 50, with amplitude modulation of the resulting ultrasound beam signal 52. When the signal is at full strength, cavitation will result, shown at region 54, while when the ultrasound beam signal is at a low point, shown in region 56, there will be no cavitation, but streaming will still occur. The amplitude-modulated beams will proceed to interact with the bubble slurry 58, producing cleaning of the teeth 59. Typically, the modulation will be in the form of a rectangular wave with a non-zero base line and a selected duty factor, which can vary. However, the modulation signal could be other configurations as well, including a triangle wave, sine wave or other arbitrary shape, and need not be periodic.

Figure 5:
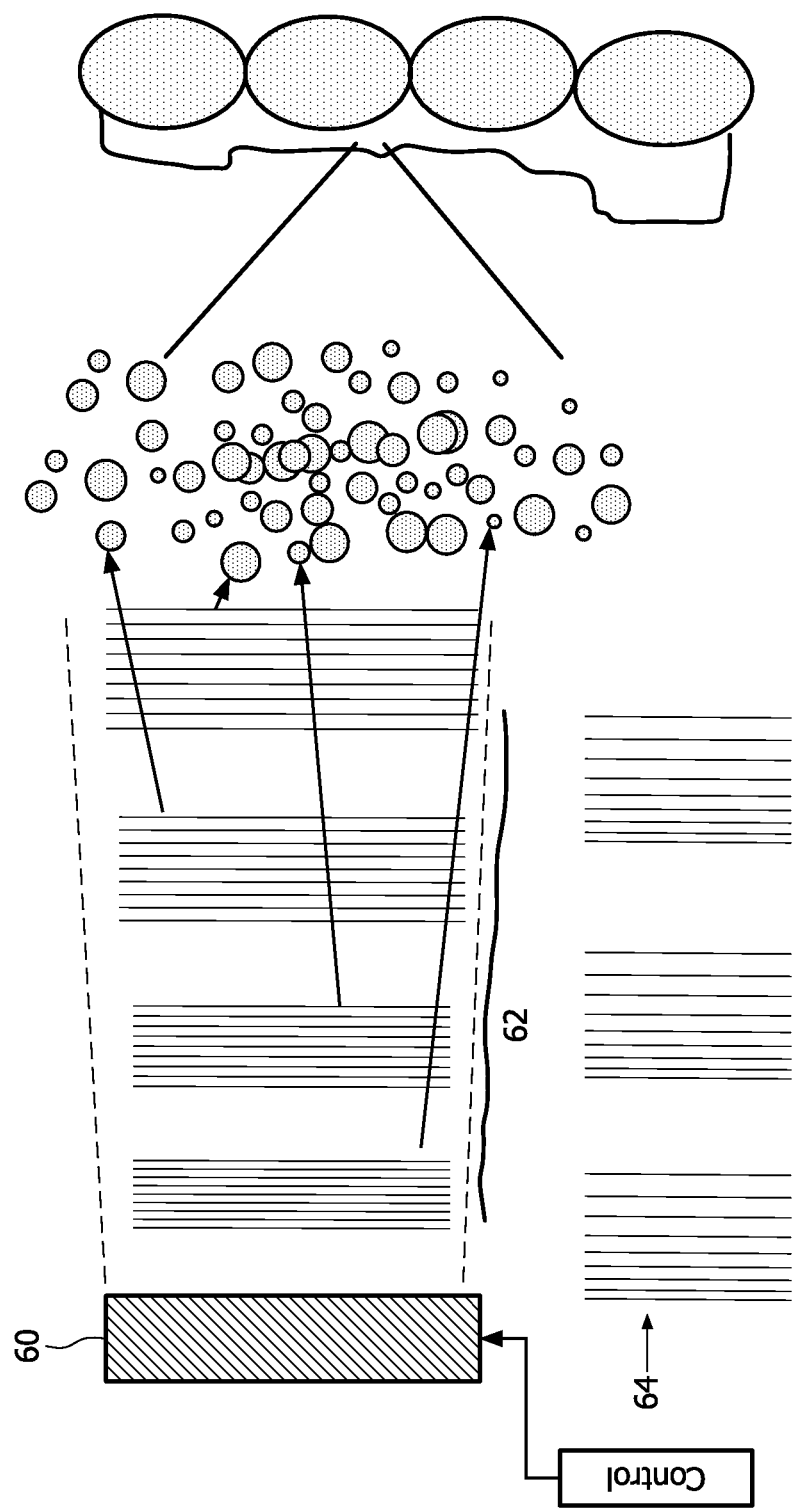
FIG. 5 is a diagram showing two frequency diversity (frequency modulation) arrangements for the ultrasound/microbubble system.

FIG. 5 shows a third optional aspect of the system, referred to as frequency diversity, which is a frequency modulation of the ultrasound beams, provided in control unit 61. Transducer or transducer array 60 produces an ultrasound beam or beams, in which the frequency varies with time, shown at 62 and 64. In 62, succeeding bursts are at different frequencies, while in 64, the frequency is varied within each burst (chirp). Transducer or transducer array 60 is a broadband transducer capable of generating frequencies over a broad range, e.g. 200-400 KHz. Such transducers are well known generally, particularly in the diagnostic medical ultrasound arena. Possibilities include double quarter wave matched piezoelectric bulk transducers, piezoelectric micro machined ultrasound transducers (pMUTs), electromagnetic acoustic transducers (eMATs) and capacitive micro machined ultrasound transducers (cMUTs). The advantage of frequency modulating the beams is that microbubbles typically have a wide range of size, and each size has a particular resonant frequency at which it oscillates and eventually breaks to produce cleaning of teeth. The oscillation of the bubbles is in response to a particular frequency. With a single ultrasound frequency, only a relatively few bubbles will vibrate and produce a cleaning effect. When a range of frequencies is produced by frequency modulation, a wide range of bubble sizes can be excited, thus utilizing many or even most of the available bubbles. In operation, a larger percentage of them are excited, producing a more effective, robust cleaning effect.

Further, the frequency variations in the ultrasound signal produced by the frequency modulation will cause the peaks and nulls of the interference pattern of the ultrasound field to sweep across the surfaces of the teeth, producing the same coverage benefit as described above with respect to spatial diversity (amplitude modulation). The excitation frequency can be varied over the bandwidth of the transducer by means of a linear, sawtooth, sinusoidal or other FM chirp function applied through the circuits that excite the transducer elements. As indicated above, one frequency range could be 200-400 KHz, thus giving a size range ratio of 2:1. An even larger ratio (3:1) could be accomplished with a range of 150-450 KHz.

As indicated above, any one of the three above features can be used in any dental cleaning appliance, either a toothbrush or a mouthpiece and produce a significant improvement in cleaning. Two features can be used as well as all three. In one particular arrangement, a single dimension (coplanar) array of cMUT transducers operating over a frequency range of 200-400 KHz can be used. A transducer array might encompass eight or more, preferably 16 or more elements, facing the teeth at the base of the bristles of a toothbrush. Located nearby or among the bristles are the means to generate the air microbubbles or conduits for movement of fluid precharged with the bubbles from another location.

As indicated above, independent electrical excitation can be provided for each element in the array or portions of the array, such that the frequency, amplitude and phase of the beams can be controlled independently for each element. The control system thus provides the effects as described above. The bubble-charged fluid provides the propagation medium and delivers the cleaning bubbles to the teeth surfaces. With the above systems, a larger fraction of the bubbles are effective in cleaning the teeth surfaces. Furthermore, the bubbles reach generally all parts of the teeth surfaces for effective cleaning, as well as the interproximal surfaces between the teeth and below the gum line.

Accordingly, a system has been disclosed which improves the action of ultrasound with microbubbles for cleaning of dental surfaces. The systems include spatial, temporal and frequency diversity to achieve the improved cleaning function and can be part of a toothbrush or mouthguard having a scrubbing capability or can be used alone.

Although a preferred embodiment of the invention has been disclosed for purposes of illustration, it should be understood that various changes, modifications and substitutions may be incorporated in the embodiment without departing from the spirit of the invention, which is defined by the claims which follow.

The invention claimed is:

1. An appliance for cleaning teeth, comprising:
an appliance body (12);
a system for producing a slurry of microbubbles (20) and directing them to the region of the teeth to be cleaned; and
a system for producing ultrasound signal beams (22) with a frequency in the range of 100 KHz to 1 MHz, directed to and in said frequency range for actuating the microbubbles for cleaning, wherein the system for producing the ultrasound signals includes (a) an array of transducer elements (40) to produce the ultrasound signals; wherein some of the transducer elements are separately power driven to provide separate power control over their associated ultrasound signals, and at least one of the following: (b) an amplitude modulation assembly (51) for modulating the amplitude of the ultrasound signals in accordance with an amplitude modulation signal; and (c) a frequency modulation system (61) for changing the frequency of the ultrasound signals over a predetermined frequency modulation range in accordance with a frequency modulation signal.

2. The appliance of claim 1, wherein the appliance includes an assembly (48) for steering the ultrasound signals by phase modulation thereof.

3. The appliance of claim 2, wherein the transducer array includes six to eight individual transducer elements and each transducer element is individually power driven to provide power control over the ultrasound beams.

4. The appliance of claim 1, wherein the appliance includes all of (a), (b) and (c).

5. The appliance of claim 1, wherein the appliance is in the form of a toothbrush (10).

6. The appliance of claim 1, wherein the appliance is in the form of a mouthpiece (26).

7. The appliance of claim 1, wherein the appliance includes (b) and wherein the amplitude modulation decreases the power of the ultrasound beams to 50% or less of maximum power.

8. The appliance of claim 7, wherein the power of the ultrasound beams at their lowest level is low enough to permit replenishment of the microbubbles, but not so low as to cut off streaming effect of the microbubbles.

9. The appliance of claim 1, wherein the appliance includes bristles (16).

10. The appliance of claim 9, wherein the appliance is a manual appliance.

11. The appliance of claim 9, wherein the appliance includes a power system (18) for moving the bristles to produce a scrubbing action on the teeth.

12. The appliance of claim 1, wherein the appliance includes (c) and the frequency modulation covers a range of 200-400 KHz.

13. The appliance of claim 1, wherein the appliance includes (c) with a modulation frequency of approximately 0.01%-1% of the ultrasound frequency.

14. The appliance of claim 1, wherein the appliance is a power toothbrush with bristles mounted on a brushhead and wherein the array of transducer elements (24) is mounted on the brushhead at the base of the bristles and wherein the microbubbles are generated in the vicinity of the brushhead.

15. The appliance of claim 1, wherein the system for producing a slurry of microbubbles is separate from the system for producing ultrasound signal beams and, when the appliance is in the form of a toothbrush, any action of toothbrush bristles thereon.

* * * * *